United States Patent [19]

Witt et al.

[11] Patent Number: 5,779,995
[45] Date of Patent: Jul. 14, 1998

[54] SLUDGE PHASE REACTOR AND PROCESS FOR PERFORMING SLUDGE PHASE REACTIONS

[75] Inventors: Harro Witt, Kuden; Uwe Jens Zarnack, Brunsbüttel; Heiko Beckhaus, Leverkusen, all of Germany

[73] Assignee: Bayer Aktiengesellschaft, Leverkusen, Germany

[21] Appl. No.: 809,840

[22] PCT Filed: Sep. 25, 1995

[86] PCT No.: PCT/EP95/03786

§ 371 Date: Apr. 2, 1997

§ 102(e) Date: Apr. 2, 1997

[87] PCT Pub. No.: WO96/11052

PCT Pub. Date: Apr. 18, 1996

[30] Foreign Application Priority Data

Oct. 7, 1994 [DE] Germany .................. 44 35 839.3

[51] Int. Cl.⁶ .................. B01J 8/22; B01J 19/00

[52] U.S. Cl. .................. 422/215; 422/224; 422/225; 422/227

[58] Field of Search .................. 422/215, 225, 422/224, 227

[56] References Cited

U.S. PATENT DOCUMENTS

| | | | |
|---|---|---|---|
| 3,761,521 | 9/1973 | Alheritiere et al. | 260/580 |
| 4,882,283 | 11/1989 | Gentry | 435/316 |
| 5,563,296 | 10/1996 | Zarnack et al. | 564/422 |

*Primary Examiner*—Nina Bhat
*Attorney, Agent, or Firm*—Joseph C. Gil; Noland J. Cheung

[57] ABSTRACT

A reactor is described for exothermic sludge phase reactions which comprises as the heat exchanger an annular chamber which is covered at the top and the bottom by the reaction mass in the reactor, the annular chamber comprising a plurality of vertical passage ducts having a circular cross-section for the reaction mass, and the coolant flowing through the annular chamber between the passage ducts for the reaction mass.

4 Claims, 2 Drawing Sheets

SLUDGE PHASE REACTOR AND PROCESS FOR PERFORMING SLUDGE PHASE REACTIONS

This continuation-in-part application, which is designated for filing in the United States, corresponds to PCT Application number PCT/EP 95/03786, which was filed on Sep. 25, 1995 and claims priority over DE Application No. P 44 35 839.3, which was filed on Oct. 7, 1994.

BACKGROUND OF THE INVENTION

Sludge phase reactions are reactions in which at least one finely divided solid phase and one fluid phase participate.

Highly exothermic sludge phase reactions require effective discharge of the heat of reaction. Sludge phase reactors therefore thus generally include expensive heat exchanger constructions inside the reaction container (see, e.g., U.S. Pat. No. 3,243,268 or European patent 263,935). In the case of the known sludge phase reactors, the heat exchange is brought about as a result of the fact that the reaction mass is pumped around so-called "field" heat exchanger pipes or boiler pipes which are closed at one end and in which the heat-transfer medium and the resultant steam are guided counter-currently. The disadvantage of this type of heat exchange is the flow speed of the reaction mass which differs in relation to the reactor chamber and the low degree of efficiency of the heat exchanger brought about thereby. The different flow speed of the reaction mass gives rise to areas in which the flow is substantially decreased and the solid components involved in the reaction can be deposited.

DESCRIPTION OF THE INVENTION

Figure 1:
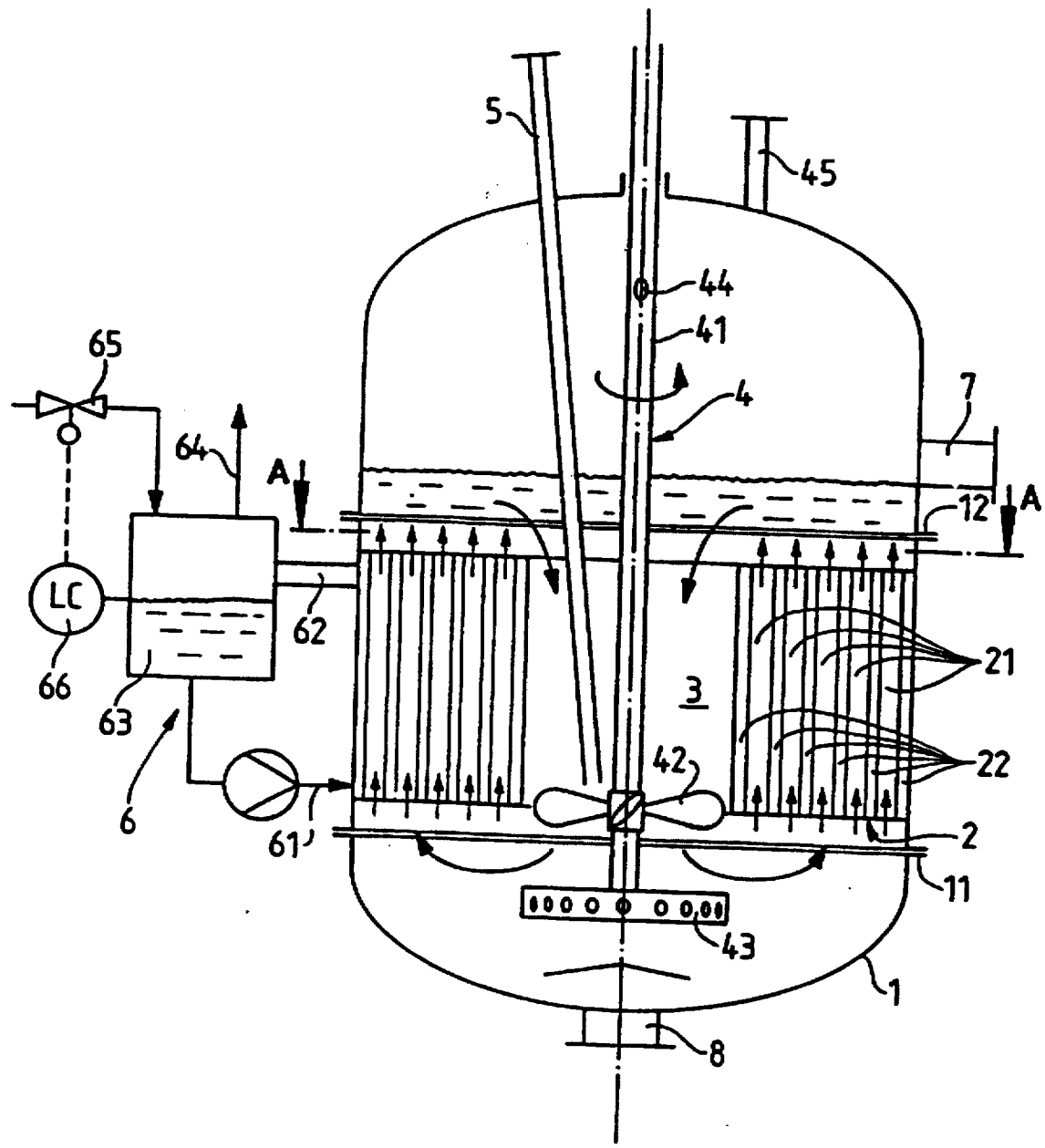
FIG. 1 shows a cross-section through the sludge phase reactor according to the invention.

In accordance with the invention it is now proposed to provide as a heat exchanger a container through which the heat-transfer medium essentially flows in one direction only, the container being equipped with a plurality of passage ducts having a circular cross-section for the reaction mass. In accordance with the invention the reaction mass is consequently guided "inversely" in the heat exchanger in comparison with conventional evaporation- heat exchangers.

The subject matter of the present invention is a sludge phase reactor for exothermic sludge phase reactions, comprising the following components:

a) a reaction container;

b) a heat exchanger in the form of an annular chamber through which the coolant and the reaction mass flow inside the reaction container, the annular chamber being covered at the top and bottom by the reaction mass;

c) a central free flow chamber inside the annular chamber for the return flow of the reaction mass;

d) a central agitator which circulates the reaction mass between the central free flow chamber and the annular chamber;

wherein the annular chamber comprises a plurality of vertical passage ducts having a circular cross-section for the reaction mass, and the coolant flows through the annular chamber between the passage ducts for the reaction mass.

Preferably reaction mass and heat-transfer medium flow through the heat exchanger annular chamber substantially in the same direction. In particular the passage ducts for the reaction mass through the annular chamber are flowed through vertically upwards. In this case the agitator is preferably disposed at the lower outlet of the central free flow chamber. At least one of the reaction components is delivered in the immediate vicinity of the agitator such that firstly the reaction component is rapidly distributed in the reaction mass and secondly the delivered reaction component with the reaction mass is introduced very rapidly into the heat exchanger.

In order for the reaction to be performed continuously, an overflow from which reacted reaction mass can be continuously drawn off is provided above the fluid level in the reaction container.

Preferably a substance which evaporates at the reaction temperature and which is delivered in liquid form at the base of the heat exchanger annular chamber and is drawn off in gaseous form from the head of the heat exchanger annular chamber is used as the heat-transfer medium. Particularly preferably, water is used as the heat-transfer medium and the heat exchange takes place with the production of steam. The coolant temperature is preferably set by maintaining the pressure of the steam produced.

Preferably reactions involving a gas phase are performed in the sludge phase reactor according to the invention. To this end the agitator is in the form of a gassing agitator or comprises an additional gassing component.

The sludge phase reactor according to the invention and having a gassing agitator is particularly suitable for performing the sludge phase hydrogenation of aromatic nitro compounds, particularly preferably for the hydrogenation of dinitrotoluenes with the production of the corresponding diamines.

The invention will be explained in greater detail with reference to the attached drawings.

The reactor according to FIG. 1 comprises a reaction container 1 which is constructed from three parts which are flanged together by means of flanges 11 and 12. The central part of the reaction container 1 contains the annular heat exchanger 2 which comprises an annular chamber closed on all sides and is penetrated by a plurality of passage pipes 21 through which the reaction mass flows rising in the direction indicated by the arrows. Located in the remaining space 22 of the annular chamber 2 is the heat-exchanger medium. As indicated by arrows, the return flow of the reaction mass is through the central free flow chamber 3 inside the annular heat exchanger 2. The circulating flow of the reaction mass is brought about by the agitator 4 with a central agitator shaft 41, driven externally of the reactor, and an agitator blade 42. In this respect the agitator blade 42 is disposed at the bottom, at the level of the outlet from the central flow chamber 3. In the embodiment illustrated the agitator shaft 41 is in the form of a hollow shaft and comprises a gassing device 43 below the agitator blade 42. The gas for gassing the reaction mass is drawn out of the gas chamber in the upper part of the reaction container 1 by means of intake openings 44 in the agitator shaft 41. A predetermined gas pressure is ensured via the gas delivery connection 45. When the reactor according to the invention is used as preferred for hydrogenating aromatic nitro compounds, hydrogen is used at a pressure of between 10 and 40 bar. More advantageously, fresh hydrogen can be delivered directly into the reaction mass. The aromatic nitro compound is introduced via delivery line 5 into the immediate vicinity of the agitator blade 42. Precious metals or nickel for example on carrier particles such as carbon, $SiO_2$, $Al_2O_3$ and the like or Raney-nickel catalysts are dispersed in the reaction mass as the finely divided solid phase. The product is continuously drawn off at the overflow 7 so that a constant fluid level is maintained. The heat exchanger annular chamber is further supplied from a heat exchanger medium circuit 6. The heat exchanger medium, preferably water just below boiling point, is introduced into the bottom of the heat exchanger at 61. Steam emerges from the top of the heat exchanger at 62 and is delivered to the steam separator 63. The arrow 64 indicates the discharge of the steam for the recovery of energy. The cooling water inflow valve 65 is controlled by means of a level regulating device 66 for the water level in the steam separator 63. When the reactor according to the invention is used as preferred for hydrogenating aromatic nitro compounds, the coolant pressure 64 is regulated so that a temperature of 120° to 250° C. is maintained in the reactor.

Figure 2:
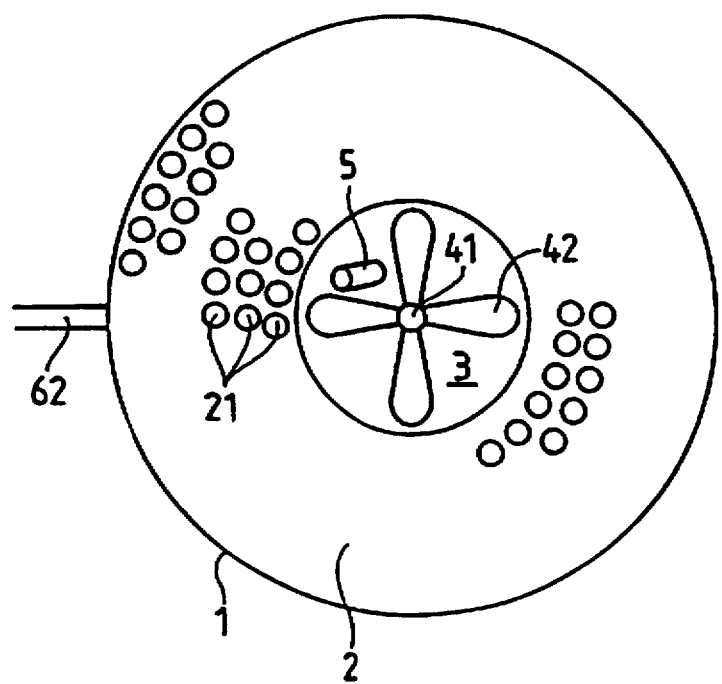
FIG. 2 shows is a cross-sectional view of the reactor of FIG. 1 in the direction of A—A of FIG. 1.

The numerals in FIG. 2 designate the same components as in FIG. 1. Only some of the passage pipes 21 are shown. The heat exchanger 2 can comprise between 100 and 3000 passage pipes 21 depending on the nominal width of the pipes (25–10 mm) and the diameter of the heat exchanger (up to 3 m).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A sludge phase reactor for exothermic sludge phase reactions comprising:

(a) a reaction container;

(b) a heat exchanger disposed within said reaction container, said heat exchanger in the form of an annular chamber through which heat-exchanging medium and reaction mass flow;

(c) wherein said annular chamber comprises a plurality of open-ended vertical passage ducts having a circular cross-section for said reaction mass, and wherein said heat-exchanging medium flows through said annular chamber between said passage ducts for said reaction mass;

(d) a central free flow chamber inside the annular chamber for the return flow of the reaction mass;

(e) a central agitator which circulates the reaction mass between the central free flow chamber and the annular chamber;

(f) wherein said agitator is additionally in the form of a gassing agitator; and (g) wherein said agitator conveys said reaction mass downwards in said central flow chamber and produces an upward flow in said vertical passage ducts.

2. The sludge phase reactor of claim 1, wherein the agitator is disposed at the outlet of the central free flow chamber and is formed with accessible walls.

3. The sludge phase reactor of claim 1, wherein at least one reacting agent is introduced into the reaction mass in the immediate vicinity of the agitator.

4. A sludge phase reactor according to claim 1, wherein said heat exchanging medium and said reaction mass flow through said annular chamber in substantially the same direction.

* * * * *